United States Patent [19]

Watanabe et al.

[11] Patent Number: 4,941,455
[45] Date of Patent: Jul. 17, 1990

[54] ENDOSCOPE HAVING BENDING MEANS

[75] Inventors: Yoshio Watanabe, Kawaguchi; Toshio Chikama, Tokyo, both of Japan

[73] Assignee: Kabushiki Kaisha Machida Seisakusho, Tokyo, Japan

[21] Appl. No.: 407,314

[22] Filed: Sep. 14, 1989

[30] Foreign Application Priority Data

Jul. 5, 1989 [JP] Japan ................................. 1-171968

[51] Int. Cl.⁵ .............................................. A61B 1/00
[52] U.S. Cl. ......................................................... 128/4
[58] Field of Search ............................................. 128/4

[56] References Cited

U.S. PATENT DOCUMENTS

| 4,718,407 | 1/1988 | Chikama | 128/4 |
| 4,721,099 | 1/1988 | Chikama | 128/4 |
| 4,773,395 | 9/1988 | Suzuki et al. | 128/4 |
| 4,834,069 | 5/1989 | Umeda | 128/4 |
| 4,841,950 | 6/1989 | Fukuda | 128/4 |

FOREIGN PATENT DOCUMENTS 56-121532 9/1981 Japan .

Primary Examiner—William H. Grieb
Attorney, Agent, or Firm—Wegner & Bretschneider

[57] ABSTRACT

There is disclosed an endoscope incorporating a device for bending a bendable portion of the endoscope. A pair of operating wires are fixedly connected at their distal ends to a distal end of the bendable portion, and are extended respectively around a pair of engaging members. The proximal ends of the operating wires are retained by a retaining member. When an operating shaft, operatively connected to the engaging members through a connecting member, is angularly moved, one of the two engaging members is moved away from the bendable portion. As a result, one of the operating wires associated with the one engaging member is pulled to bend the bendable portion. Alternatively, first and second operating shafts, four operating wires and four engaging members can be employed so that the bendable portion can be bent in two directions generally perpendicular to each other. In this case, the engaging members are moved upon angular movement of the first operating shaft, and the turned-back portions of the four operating wires are moved upon angular movement of the second operating shaft, so as to simultaneously pull two out of the four operating wires, thereby bending the bendable portion.

9 Claims, 6 Drawing Sheets

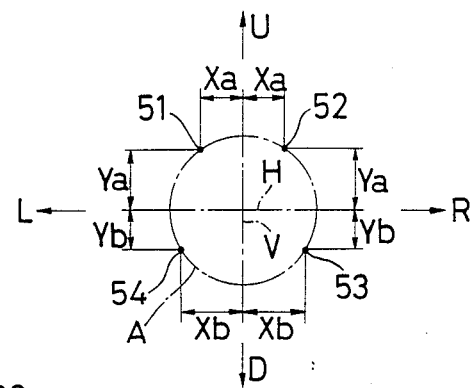
Fig. 10
Fig. 9
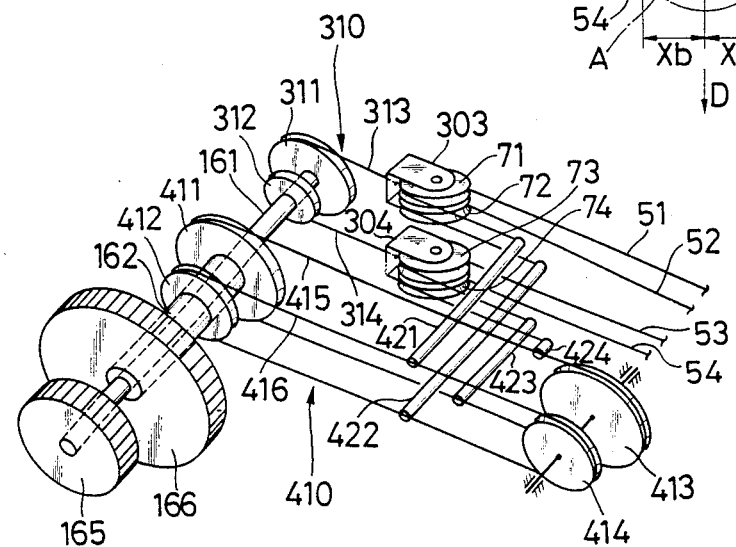
Fig. 11
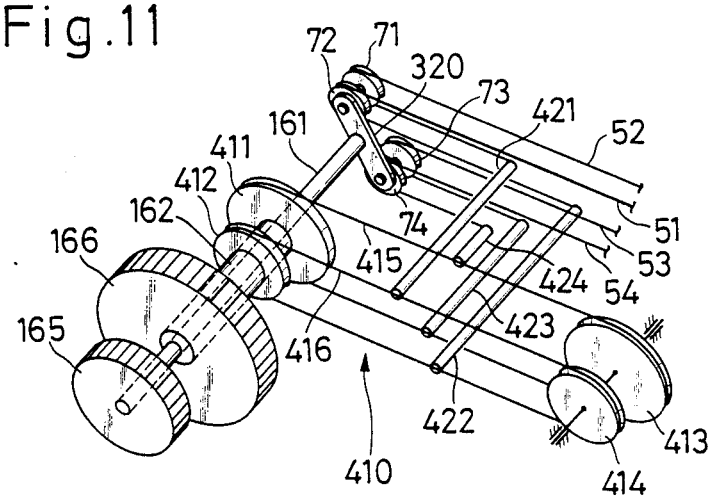

ENDOSCOPE HAVING BENDING MEANS

BACKGROUND OF THE INVENTION

1. Field of the Invention

This invention relates generally to an endoscope, and more particularly an endoscope incorporating a device for bending a bendable portion of the endoscope.

2. Prior Art

Generally, an endoscope includes a body, an insertion portion extending from the body, and a bendable portion extending from a forward end of the insertion portion. Devices for bending such a bendable portion are disclosed in U.S. Pat. Nos. 4,718,407, 4,721,099 and 4,834,069, and such a device includes one or two pairs of operating wires. These operating wires are passed through the insertion portion and the bendable portion, and are connected at their distal ends to the distal end of the bendable portion in spaced relation to each other. The proximal end portions of the operating wires are received in the body of the endoscope. One or two operating shafts are mounted on the body, and a manipulating member is mounted on one end of the operating shaft, extending exteriorly of the body, so as to angularly move the operating shaft. A pulley is fixedly mounted on the operating shaft, and each pair of operating wires are fixedly connected at their proximal ends to the peripheral surface of the pulley. When the operating shaft is angularly moved, one of the pair of operating wires associated therewith is pulled, so that the bendable portion is bent or flexed.

Among the users, there has now been a demand that the bendable portion can be bent to a large extent with a small amount of angular movement of the manipulating member in order to rapidly bend the bendable portion to a desired extent. However, the devices for bending the bendable portion of the endoscope, as disclosed in the above-mentioned U. S. patents, have failed to meet this demand. The reason for this will now be described. The amount of bending of the bendable portion is determined by the amount of movement of the proximal ends of the pulled operating wire, and this amount of movement is equal to the amount of angular movement of the outer periphery of the pulley. Therefore, in order to meet the above demand, it is necessary to increase the diameter of the pulley, and this results in an increased size of the body. However, the increase in size of the body is limited, because with the increase in the body size, the operator is susceptible to fatigue when operating the bendable device.

In such a construction as disclosed in the above-mentioned U.S. patents, in which the bendable portion can be bent by pulling a selected one of the operating wires, there is a possibility that the bendable portion may be bent in a twisted manner. The reason for this is that an optical fiber bundle, tubes and other elements which are different in rigidity are received asymmetrically in the bendable portion, so that these component parts offer uneven resistances to the bendable portion when the bendable portion is being bent. To overcome this difficulty, Japanese Laid-Open (Kokai) Patent Application No. 121532/81 has proposed a bending device in which two out of four operating wires are to be pulled simultaneously. More specifically, the first, second, third and fourth operating wires are fixedly connected at their distal ends to the distal end of the bendable portion in such a manner that these fixed distal ends of the four operating wires are disposed in this order on a circle, lying in a plane perpendicular to the axis of the bendable portion, and are circumferentially spaced from one another. Connecting members are connected to the proximal ends of the operating wires, respectively, and each connecting member has a pair of first and second holes formed therethrough. A pair of pulleys are fixedly mounted on each of two operating shafts, and a pair of driving wires are fixedly connected at their one ends to the diametrically opposite portions of the outer peripheral surface of each of the pulleys, respectively, and extend from the pulley toward the bendable portion. The four driving wires operable by one of the operating shafts are passed respectively through the first holes in the four connecting members whereas the other four driving wires operable by the other operating shaft are passed respectively through the second holes in the four connecting members. A stop member is fixedly connected to the other end of each of the driving wires.

In this conventional device of the above Japanese Laid-Open Patent Application No. 121532/81, the following function is intended. When one of the operating shafts is angularly moved together with the pair of pulleys mounted thereon, the first and second operating wires or the third and fourth operating wires are pulled simultaneously through two of the driving wires connected to these pulleys and also through two of the connecting members with which the stop members, mounted respectively on these two driving wires, are engaged. As a result, the bendable portion is bent upwardly or downwardly. On the other hand, when the other operating shaft is angularly moved, the second and third operating wires or the first and fourth operating wires are pulled simultaneously to bend the bendable portion in a left-hand direction or in a right-hand direction.

In this conventional device, when the bendable portion is not in its bent condition, the stop members abut against the end faces of the connecting members, respectively, and therefore actually the bendable portion can not be bent as desired. More specifically, when one of the operating shafts is angularly moved together with the two pulleys mounted thereon, so as to pull, for example, the two driving wires connected respectively to the lower sides of these two pulleys, the two connecting members, with which the stop members on these two driving wires are engaged, try to move away from the bendable portion to pull the two operating wires, connected to these two connective members, so as to bend the bendable portion, for example, downwardly. At this time, although the other two operating wires connected respectively to the other two connecting members are pulled by the bendable portion, these two operating wires can not be moved toward the bendable portion. The reason is that these two connecting members are prevented from movement by the stop members connected to those driving wires operatively associated with the other operating shaft remaining stationary. As a result, the bendable portion is prevented from being bent.

As is clear from the foregoing, in the device of the above-mentioned Japanese Laid-Open Patent Application No. 121532/81, when the bendable portion is to be bent, it is necessary that all the stop members connected respectively to the driving wires be spaced apart from their mating connecting members, respectively, while maintaining the bendable portion in a straight condition. However, when such spacing or play is provided, the operating wires can not be pulled at an initial stage of the angular movement of the operating shaft, so that the bendable portion can not be bent at this initial stage, thus adversely affecting the operability.

SUMMARY OF THE INVENTION

It is therefore an object of this invention to provide an endoscope incorporating a device for bending a bendable portion of an endoscope which device will not increase the size of a body of the endoscope, and can bend the bendable portion to a large extent with a small amount of manipulation of a manipulating member.

Another object is to provide such a bending device which can bend the bendable portion without twisting it, and is excellent in operability.

According to a first aspect of the present invention, there is provided an endoscope comprising:

(a) a body;

(b) a hollow insertion portion extending from said body;

(c) a hollow elongated bendable portion extending from a forward end of said insertion portion remote from said body; and (d) means for bending said bendable portion, said bending means comprising:

(i) a pair of operating wires having their proximal ends disposed within said body, said two operating wires extending through said insertion portion into said bendable portion and fixedly connected at their distal ends to a distal end of said bendable portion remote from said insertion portion, said fixed distal ends of said two operating wires being spaced from each other generally peripherally of said bendable portion;

(ii) an operating shaft mounted on said body for angular movement about an axis thereof;

(iii) an manipulating member for angularly moving said operating shaft;

(iv) a pair of engaging members provided at said body, said pair of operating wires being extended respectively around said pair of engaging members to be turned back toward said bendable portion;

(v) retainer means retaining the proximal ends of said pair of operating wires; and (vi) connecting means operatively connecting said operating shaft to said pair of engaging members so that when said operating shaft is angularly moved in one direction, one of said pair of engaging members can be moved away from said bendable portion, with the other engaging member being moved toward said bendable portion, so as to pull said operating wire, associated with said one engaging member, away from said bendable portion, thereby bending said bendable portion in one direction; when said operating shaft is angularly moved in the other direction, said other engaging member being moved away from said bendable portion through said connecting means, with said one engaging member being moved toward said bendable portion, so as to pull said operating wire, associated with said other engaging member, away from said bendable portion, thereby bending said bendable portion in another direction.

According to a second aspect of the present invention, there is provided an endoscope comprising:

(a) a body;

(b) a hollow insertion portion extending from said body;

(c) a hollow elongated bendable portion extending from a forward end of said insertion portion remote from said body; and (d) means for bending said bendable portion, said bending means comprising:

(i) first to fourth operating wires having their proximal ends disposed within said body, said four operating wires extending through said insertion portion into said bendable portion and fixedly connected at their distal ends to a distal end of said bendable portion remote from said insertion portion, said fixed distal ends of said first to fourth operating wires being spaced from one another peripherally of said bendable portion and arranged in this order;

(ii) a pair of first and second operating shafts mounted on said body for angular movement about their axes;

(iii) a pair of first and second manipulating members for angularly moving said first and second operating shafts, respectively;

(iv) first to fourth main engaging members provided at said body, said first to fourth operating wires being extended respectively around said first to fourth main engaging members to be turned back toward said bendable portion to provide four turned-back portions defined respectively by the proximal end portions of said four operating wires, respectively;

(v) first connecting means operatively connecting said first operating shaft to said four main engaging members so that when said first operating shaft is angularly moved in one direction, said first and second engaging members are moved away from said bendable portion so as to simultaneously pull said first and second operating wires away from said bendable portion, thereby bending said bendable portion in a first direction; when said first operating shaft is angularly moved in the other direction, said third and fourth engaging members being moved away from said bendable portion through said first connecting means so as to simultaneously pull said third and fourth operating wires away from said bendable portion, thereby bending said bendable portion in a second direction opposite to said first direction; and (vi) second connecting means operatively connecting said second operating shaft to said four turned-back portions so that when said second operating shaft is angularly moved in one direction, said turned-back portions of said first and fourth operating wires are moved toward said bendable portion so as to simultaneously pull said first and fourth operating wires away from said bendable portion, thereby bending said bendable portion in a third direction generally perpendicular to said first and second directions; when said second operating shaft is angularly moved in the other direction, said turned-back portions of said second and third operating wires being moved toward said bendable portion through said second connecting means so as to simultaneously pull said second and third operating wires away from said bendable portion, thereby bending said bendable portion in a fourth direction opposite to said third direction.

BRIEF DESCRIPTION OF THE DRAWINGS

FIGS. 8 and 9 are perspective views of bending devices of fifth and sixth embodiments of the invention, respectively;

FIG. 10 is a schematic view showing the positions of fixed distal ends of four operating wires of the bending device of FIG. 9;

FIGS. 11 and 12 are perspective views of bending device of seventh and eighth embodiments of the invention, respectively.

DESCRIPTION OF THE PREFERRED EMBODIMENTS OF THE INVENTION

The present invention will now be described with reference to the drawings.

Figure 1:
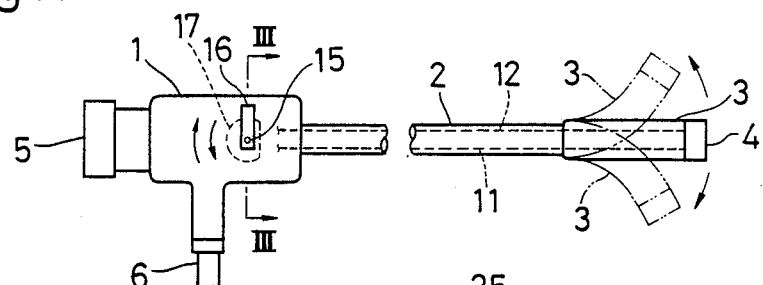
FIG. 1 is a front-elevational view of an endoscope incorporating a bending device, according to a first embodiment of the present invention, with a part omitted.
Figure 2:
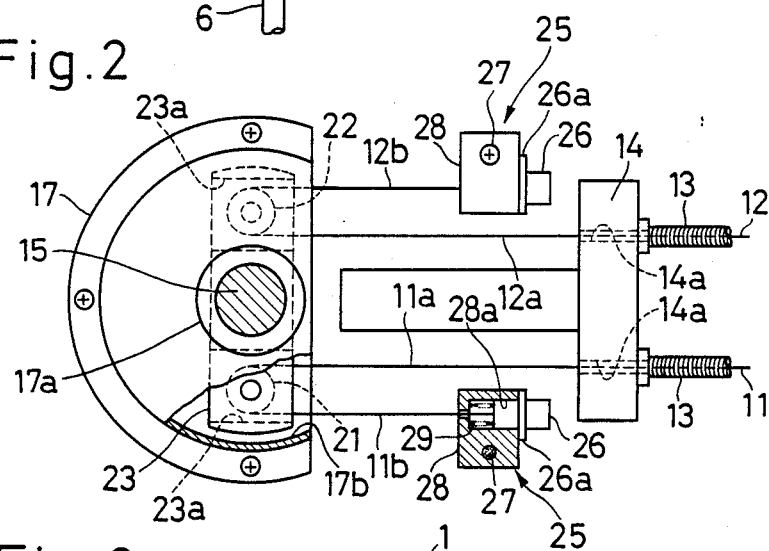
FIG. 2 is an enlarged front-elevational view of the bending device.
Figure 3:
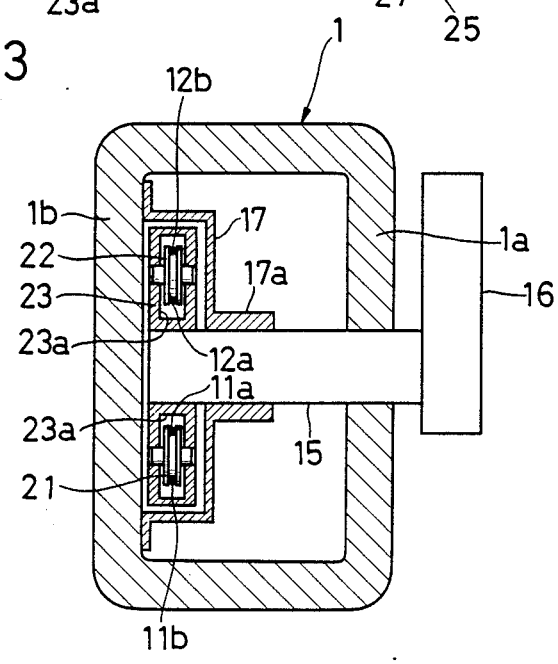
FIG. 3 is a cross-sectional view taken along the line III—III of FIG. 1.

FIGS. 1 to 3 shows a first preferred embodiment of an endoscope of the present invention. The endoscope shown in FIG. 1 comprises a hollow body 1, and an insertion portion 2 extending from a distal end of the body 1, the insertion portion 2 being in the form of a tube and being adapted to be inserted into a body cavity in a human body. A bendable portion 3 in the form of a tube extends from a distal end of the insertion portion 2 coaxially therewith. A rigid portion 4 of a circular cross-section is fixedly mounted on the distal end of the bendable portion 3. The rigid portion 4 has an illumination window and a viewing window both of which are not shown in the drawings. An ocular portion 5 is mounted on the proximal end of the body 1. The ocular portion 5 is optically connected to the above viewing window through an image transmitting optical system (not shown) including a bundle of optical fibers, so that the body cavity can be viewed or observed from the ocular portion 5. A cable 6 is connected at one end to the body 1, and the other end of the cable 6 is connected to a light source. Light from this light source is supplied to the body cavity via the optical fiber bundle passing through the cable 6, the body 1, the insertion portion 2 and the bendable portion 3.

The bendable portion 3 can be bent by a bending device. More specifically, this bending device comprises two operating wires 11 and 12 passed through the insertion portion 2 and the bendable portion 3. The distal ends of the two operating wires 11 and 12 are fixedly connected respectively to the upper and lower sections of the rigid portion 4 mounted on the distal end of the bendable portion 3. These two fixed distal ends of the wires 11 and 12 are spaced equidistantly from the axis or center line of the rigid portion 4 and are spaced an angle of 180 degrees from each other circumferentially of the rigid portion 4, that is, in diametrically opposite relation to each other. The proximal ends of the operating wires 11 and 12 are disposed in the body 1.

As shown in FIG. 2, the operating wires 11 and 12 are inserted respectively in flexible tubes 13 and 13 each composed of a helically wound metal wire. The flexible tubes 13 and 13 are inserted in the insertion portion 2, and their distal ends are fixedly connected to the upper and lower sections of the proximal end of the bendable portion 3 remote from the rigid portion 4 in such a manner that these two distal ends are circumferentially spaced an angle of 180° from each other, that is, in diametrically opposite relation to each other. The proximal ends of the flexible tubes 13 and 13 are fixedly connected to a wire guide 14 fixedly mounted within the body 1. The wire guide 14 has a pair of holes 14a and 14a formed therethrough and extending in the direction of the axis of the insertion portion 2. The operating wires 11 and 12 are passed respectively through the two holes 14a and 14a so as to slidingly move therealong. By pulling the proximal end portion of one operating wire 11 extending from the wire guide 14 away from the insertion portion 2, the bendable portion 3 is bent downwardly. Also, by pulling the proximal end portion of the other operating wire 12 extending from the wire guide 14 away from the insertion portion 2, the bendable portion 3 is bent upwardly.

As shown in FIG. 3, an operating shaft 15 extends through one side wall 1a of the body 1 so as to be angularly moved about its axis, and a manipulating lever (manipulating member) 16 is fixedly mounted on one end of the operating shaft 15 projecting exteriorly of the body 1. A cover 17 is fixedly secured to the inner surface of the other side wall 1b of the body 1, the cover 17 having a tubular portion 17a serving as a bearing for angularly movably supporting the operating shaft 15. The cover 17 is of a generally dish-shape, with one side thereof directed toward the insertion portion 12 being removed to provide an opening 17b.

As shown in FIGS. 2 and 3, a straight arm 23 is fixedly mounted at its central portion on the other end of the operating shaft 15 disposed within the cover 17. A pair of mounting holes 23a and 23a are formed through the opposite end portions of the arm 23 and extend in a direction perpendicular to the longitudinal axis of the arm 23. A pair of pulleys (engaging members) 21 and 22 are mounted respectively within the two mounting holes 23a and 23a so as to be angularly moved about their respective axes. The pulleys 21 and 22 are spaced from each other an angle of 180° circumferentially of the operating shaft 15, and are spaced equidistantly from the operating shaft 15. In this embodiment, the arm 23 serves as means operatively connecting the operating shaft 15 to the pulleys 21 and 22.

The proximal portions of the operating wires 11 and 12 extending from the wire guide 14 are extended respectively around the outer peripheries of the pulleys 21 and 22 over about halves of these peripheries. Thus, the proximal portion of each of the operating wires 11 and 12 has a first portion 11a (12a) (hereinafter referred to as "proximal leading portion") leading from the wire guide 14 to the pulley 21 (22), and a second or turned-back portion 11b (12b) extending from the pulley 21 (22) toward the wire guide 14. The proximal leading portions 11a and 12a are disposed in substantially parallel opposed relation to the turned-back portions 11b and 12b, respectively.

The proximal ends of the operating wires 11 and 12, that is, the ends or extremities of the turned-back portions 11b and 12b of these operating wires, are prevented respectively by retainer means 25 and 25 from moving toward the pulleys 21 and 22. More specifically, each retainer means 25 comprises a cylindrical slider 26 fixedly connected to the end of the turned-back portion 11b (12b), and a stop member 28 fastened to the inner surface of the body 1 by a screw 27. The stop member 28 has a stepped hole 28a extending in the axial direction of the insertion portion 2 and defined by a greater-diameter portion remote from the arm 23 and a smaller-diameter portion. The slider 26 is slidably received in the greater-diameter portion of the stepped hole 28, and the turned-back portion 11b (12b) of the operating wire 11 (12) extends through the smaller-diameter portion of the stepped hole 28. The slider 26 has a flange 26a formed on its outer periphery intermediate opposite ends thereof, and the flange 26a is abutted against one end face of the stop member 28 remote from the arm 23 so as to prevent the turned-back portion 11b (12b) from moving toward the pulley 21 (22). A compression spring 29 is accommodated within the greater diameter portion of the axial hole 28a of the stopper 28, and acts between a shoulder, formed between the greater-diameter and smaller-diameter portions, and one end of the slider 26 disposed in opposed relation to this shoulder. The slider 26 is urged by the compression spring 29 toward the bendable portion 3 under a relatively weak force.

In the bending device of the above construction, when the bendable portion 3 is in a straight condition as indicated by solid lines in FIG. 1, the arm 23 is disposed perpendicular to the axis of the insertion portion 2, and the flange 26a of each slider 26a is held against the end face of a respective one of the stoppers 28.

When the operating shaft 15 is angularly moved clockwise (FIGS. 1 and 2) together with the arm 23 by manipulating the manipulating lever 16, the lower pulley 21 is moved or displaced in a direction away from the bending portion 3 to pull the lower operating wire 11, so that the bendable portion 3 is bent downwardly as indicated in dots-and-dash lines in FIG. 1. At this time, since the end of the turned-back portion 11b is retained against movement by the retainer means 25, the proximal leading portion 11a of the lower operating wire 11, as well as that portion of the operating wire 11 passing through the hole 14a and the flexible tube 13, is moved in an amount twice the amount of movement of the pulley 11. Thus, the amount of bending of the bendable portion 3 per unit angular movement of the operating shaft 15 can be greater than that achieved in the conventional bending devices. Therefore, the bendable portion 3 can be bent rapidly.

In accordance with the above-mentioned clockwise angular movement of the operating shaft 15, the other or upper pulley 22 is moved toward the bendable portion 3, so that the proximal leading portion 12a of the operating wire 12, as well as that portion of the operating wire 12 passing through the hole 14a and the flexible tube 13, is allowed to move toward the bendable portion 3 in accordance with the downward bending movement of the bendable portion 3. The bendable portion 3 begins to be bent slightly after the pulleys 21 and 22 begin to move, and the bendable portion 3 thus bent pulls the operating wire 12 toward the bendable portion 3. Because of this time lag, the operating wire 12 tends to be temporarily loosened. However, at this time, since the slider 26 connected to the operating wire 12 is moved toward the bendable portion 3 under the influence of the spring 29 of the retainer means 25, the operating wire 12 is prevented from becoming loosened.

When the operating shaft 15 is angularly moved in a counterclockwise direction, the upper operating wire 12 is pulled through the arm 23 and the pulley 22, so that the bendable portion 3 is bent upwardly as indicated in dots-and-dash lines in FIG. 1.

Other preferred embodiments of bending devices of the present invention will now be described with reference to FIGS. 4 to 13 in which those parts corresponding to those of the first embodiment and preceding embodiment(s) are denoted by the same reference numerals, respectively, and will not be described further in detail.

Figure 4:
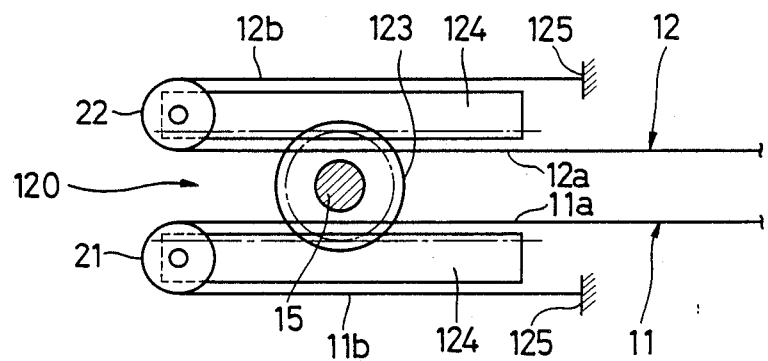
FIGS. 4 and 5 are front-elevational views of bending devices of second and third embodiments of the invention, respectively.

In a second embodiment of the invention shown in FIG. 4, a pinion or gear 123 is fixedly mounted on an operating shaft 15 for angular movement therewith. The pinion 123 is in mesh at its opposite sides with a pair of parallel spaced, opposed racks 124 and 124 mounted on the body 1 for movement along their longitudinal axes, that is, in the direction of the axis of the insertion portion 2. Pulleys 21 and 22 are rotatably mounted respectively on one ends of the pair of racks 124 and 124, and operating wires 11 and 12 are extended around the pulleys 21 and 22. In this embodiment, the pinion 123 and the racks 124 and 124 constitute connecting means 120 which operatively connects the operating shaft 15 to the pulleys 21 and 22. Although the ends of the turned-back portions 11b and 12b of the operating wires 11 and 12 may be retained by the retainer means 25 mentioned above in the first embodiment, the ends of the turned-back portions are fixedly connected to the body 1 through respective fixing members 125, as shown in FIG. 4, in which case the fixing members 125 serve as retainer means for the operating wires 11 and 12. Also, the ends of the turned-back portions 11b and 12b may be fixed directly to the body 1, in which case the body 1 serves as retainer means for the operating wires 11 and 12.

In this second embodiment of FIG. 4, when the operating shaft 15 is angularly moved in a clockwise direction together with the pinion 123, the lower rack 124 is moved, together with the pulley 21, in a direction away from the bendable portion 3 whereas the upper rack 124 is moved, together with the pulley 22, toward the bendable portion 3. As a result, the lower operating wire 11 is pulled to bend the bendable portion 3 downwardly. On the other hand, when the operating shaft 15 is angularly moved in a counterclockwise direction, the racks 124 and 124 are moved in a manner reverse to that mentioned above, so that the bendable portion 3 is bent upwardly. In this embodiment, also, the amount of movement of the proximal leading portions 11a and 12a of the operating wires 11 and 12 is twice the amount of movement of the pulleys 1 and 22, and therefore the bendable portion 3 can be bent rapidly.

Figure 5:
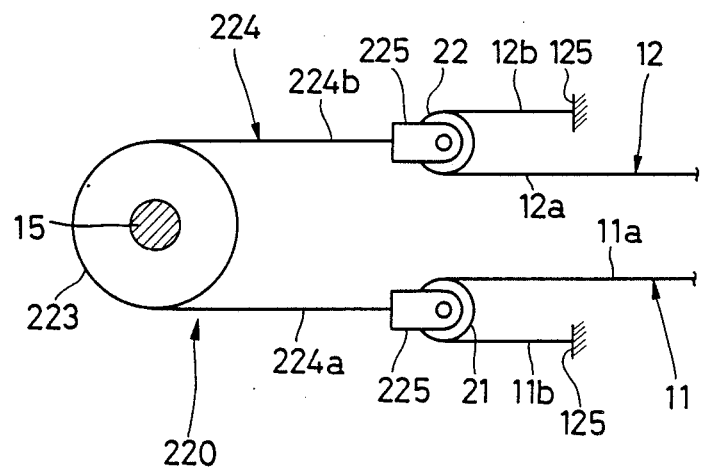

In a third embodiment of the invention shown in FIG. 5, a pulley 223 is fixedly mounted on the operating shaft 15 for angular movement therewith, and a driving wire 224 is extended around the pulley 223 so that the driving wires 224 has parallel opposed first and second portions 224a and 224b extending from the pulley 223 toward the bendable portion 3. The driving wire 224 is fixedly connected to that portion of the outer periphery of the pulley 223 remotest from the bendable portion 3. The ends of the first and second portions 224a and 224b remote from the pulley 223 are fixedly connected respectively to support members 225 and 225. Pulleys 21 and 22 are rotatably mounted on the support members 225 and 225, respectively. In this embodiment, the pulley 223 and the driving wire 224 constitute connecting means 220 which operatively connects the operating shaft 15 to the pulleys 21 and 22.

In this third embodiment of FIG. 5, when the operating shaft 15 is angularly moved, together with the pulley 223, in a clockwise direction, the lower or first portion 224a of the driving wire 224 is pulled so that the upper or second portion 224b is loosened. As a result, the support member 225 fixed to the end of the lower portion 224a is moved, together with the pulley 21, in a direction away from the bendable portion 3, so that the lower operating wire 11 is pulled to bend the bendable portion 3 downwardly. On the other hand, when the operating shaft 15 is angularly moved in a counterclockwise direction, the upper operating wire 12 is pulled toward the pulley 223 to bend the bendable portion 3 upwardly. The amount of movement of the proximal leading portions 11a and 12b of the operating wires 11 and 12 is twice the amount of movement of the pulleys 21 and 22, and therefore the bendable portion 3 can be bent rapidly.

In this embodiment of FIG. 5, the pulley 223 may be replaced by a sprocket, in which case a chain is used instead of the driving wire 224.

In the above embodiments, although the bending devices capable of bending the bendable portion 3 only in a vertical direction, that is, in upward and downward directions, have been described for the sake of simplicity of explanation, the bending devices can be so modified that the bendable portion 3 can also be bent horizontally in right-hand and left-hand directions, that is, in a direction perpendicular to the sheet of FIG. 1. In this case, in each of the above embodiments, an additional bending device of a similar construction is incorporated in the endoscope so as to bend the bendable portion 3 horizontally, and a pair of operating wires of the additional bending device are fixedly connected at their distal ends to the rigid portion 4 in diametrically opposite relation to each other, so that the fixed distal ends of these two operating wires and the fixed distal ends of the operating wires 11 and 12 are spaced an angle of 90 degrees from one another circumferentially of the rigid portion 4.

Figure 6:
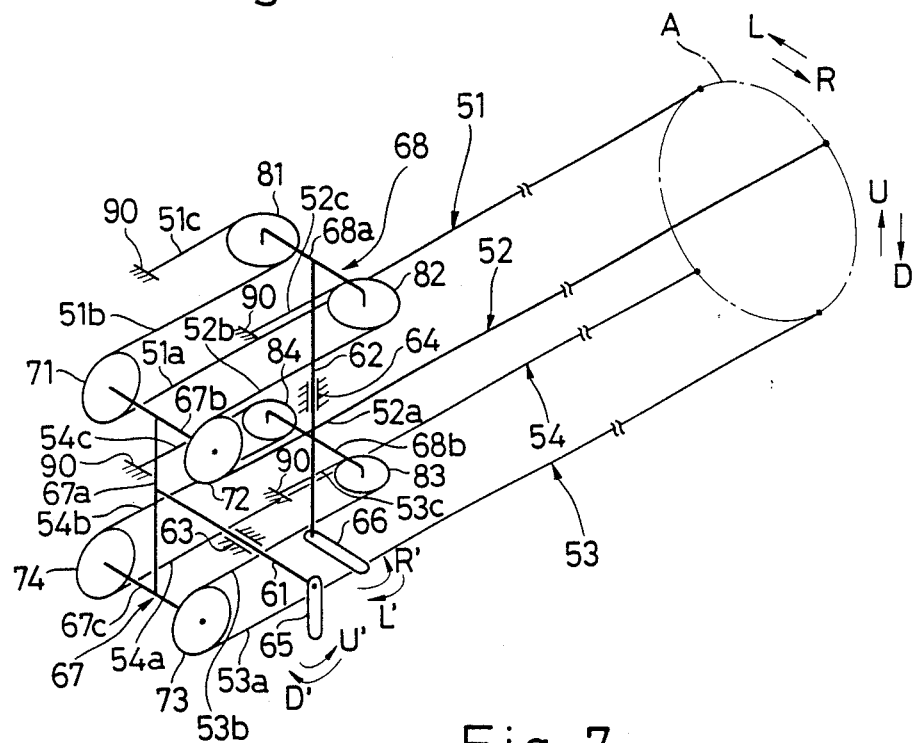
FIG. 6 is a perspective view of a bending device according to a fourth embodiment of the invention.
Figure 7:
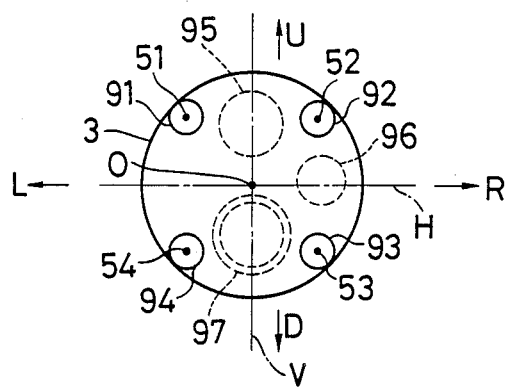
FIG. 7 is a schematic cross-sectional view of a bendable portion to be bent by the bending device of FIG. 6.

In a fourth embodiment of the invention shown in FIGS. 6 and 7, there are provided four operating wires 51 to 54, and by simultaneously pulling two out of these four operating wires, the bendable portion 3 can be bent vertically and horizontally. As shown in FIG. 7, a bundle 95 of optical fibers for transmitting an image, a bundle 96 of optical fibers for transmitting light for illumination purposes and a tube 97 for feeding water and the air are asymmetrically received in the bendable portion 3. Four rows of support members 91 to 94 are mounted within the bendable portion 3 and are arranged longitudinally of the bendable portion 3. The four operating wires 51 to 54 are supported respectively by the support members 91 to 94 and pass through the bendable portion 3.

The distal ends of the four operating wires 51 to 54 are fixedly connected to the rigid portion 4 and are circumferentially spaced an angle of 90 degrees from one another on a circle A disposed in a plane perpendicular to the axis O of the bendable portion 3. The operating wires 51 to 54 are disposed in this order in a clockwise direction (FIG. 7). More specifically, a vertical line V passes through the center of the circle A, and a horizontal line H passes through the center of the circle A, the vertical and horizontal lines V and H being disposed in the plane in which the circle A lies. The distal ends or fixed points of the operating wires 51 to 54 are spaced an angle of 45 degrees from the vertical and horizontal lines V and H circumferentially of the circle A.

The operating wires 51 to 54 are guided by respective flexible tubes and a wire guide as in the preceding embodiments.

As shown in FIG. 6, two operating shafts 61 and 62 respectively extending horizontally and vertically are passed through and angularly movably borne by a horizontally-disposed bearing 63 and a vertically-disposed bearing 64, respectively, the bearings 63 and 64 being mounted within a body (not shown) of the endoscope. The first operating shaft 61 is remoter from the bendable portion 3 than the second operating shaft 62. Manipulating levers 65 and 66 are fixedly mounted respectively on one ends of the operating shafts 6 extending exteriorly of the body.

A vertical rod 67a is fixedly secured at its central portion to the other end of the first operating shaft 61 disposed within the body, and two opposed horizontal rods 67b and 67c are fixedly secured at their central portions to the opposite ends of the rod 67a, respectively. A pair of parallel opposed pulleys (engaging members) 71 and 72 are rotatably mounted on the opposite ends of the rod 67b. Similarly, a pair of parallel opposed pulleys (engaging members) 73 and 74 are rotatably mounted on the opposite ends of the rod 67c. The rods 67a, 67b and 67c constitute first connecting means 67 which operatively connects the first operating shaft 61 to the pulleys 71 to 74.

A horizontal rod 68a is fixedly secured at its central portion to the upper end of the second operating shaft 62, and a horizontal rod 68b is fixedly secured at its central portion to the second operating shaft 62 intermediate the opposite ends of the operating shaft 62. Each of the rods 68a and 68b is directed vertically downwardly at its opposite ends. A pair of horizontally-disposed pulleys 81 and 82 are rotatably mounted on the opposite ends of the rod 68a, respectively. Similarly, a pair of horizontally-disposed pulleys 83 and 84 are rotatably mounted on the opposite ends of the rod 68b, respectively. The rods 68a and 68b constitute a second connecting means 68 which operatively connects the second operating shaft 62 to the pulleys 81 to 84.

The operating wire 51 is extended around the pulley 71 over about a half of the outer periphery of the pulley 71, and is further extended around the pulley 81 over about a half of the outer periphery thereof. The proximal end of the operating wire 51 is fixed to the body through a fixing member 90. Thus, the operating wire 51 has a proximal leading portion 51a extending between a wire guide and the pulley 71, a first turned-back portion 51b extending between the pulleys 71 and 81, and a second turned-back portion 51c extending between the pulley 81 and the fixing member 90. Similarly, the operating wire 52 is extended around the pulleys 72 and 82, and the operating wire 53 is extended around the pulleys 73 and 83, and the operating wire 54 is extended around the pulleys 74 and 84. The proximal ends of the operating wires 52, 53 and 54 are fixedly connected to fixing members 90, respectively. The operating wires 52, 53 and 54 have respective proximal leading portions 52a, 53a and 54a, respective first turned-back portions 52b, 53b and 54b and second turned-back portions 52c, 53c and 54c.

In the bending device of FIGS. 6 and 7, when the bendable portion 3 is to be bent vertically, the second operating shaft 62 is prevented from angular movement by a rotation prevention means (not shown). In this condition, when the manipulating lever 65 is manipulated to angularly move the first operating shaft 61 in a direction of an arrow U', the pulleys 71 and 72 are moved in a direction away from the bendable portion 3 whereas the pulleys 72 and 74 are moved toward the bendable portion 3. As a result, the two operating wires 51 and 52, connected at their distal ends to the rigid portion 4 above the horizontal line H, are simultaneously pulled, so that the bendable portion 3 is bent upwardly, that is, in a direction of an arrow U. When the operating shaft 61 is angularly moved in the opposite direction indicated by an arrow D', the movement of the pulleys 71 to 74 is reversed, and the two operating wires 53 and 54, connected to the rigid portion 4 below the horizontal line H, are simultaneously pulled, so that the bendable portion 3 is bent downwardly, that is, in a direction of an arrow D.

When the bendable portion 3 is to be bent horizontally, the first operating shaft 61 is prevented from angular movement by a rotation prevention means (not shown). In this condition, the manipulating lever 66 is manipulated to angularly move the second operating shaft 62 in a direction of an arrow L'. As a result, the pulleys 81 and 84 are moved toward the bendable portion 3 whereas the pulleys 82 and 83 are moved away from the bendable portion 3, so that two operating wires 51 and 54, connected at their distal ends to the rigid portion 4 on the left-hand side of the vertical line V, are pulled simultaneously to bend the bendable portion 3 in a left-hand direction indicated by an arrow L. When the second operating shaft 62 is angularly moved in the opposite direction, that is, in a direction of an arrow R', the movement of the pulleys 81 to 84 is reversed, so that the two operating wires 52 and 53, connected at their distal ends to the rigid portion 4 on the right-hand side of the vertical line V, are pulled simultaneously to bend the bendable portion 3 in a right-hand direction indicated by an arrow R.

When the bendable portion 3 is vertically bent through the angular movement of the first operating shaft 61, the amount of movement of the proximal leading portions 51a to 54a of the operating wires 51 to 54 is twice the amount of movement of the pulleys 71 to 74. Therefore, the bendable portion 3 can be rapidly bent upwardly and downwardly. Similarly, when the bendable portion 3 is horizontally bent through the second operating shaft 62, the amount of movement of the proximal leading portions 51a to 54a is twice the amount of movement of the pulleys 81 to 84. Therefore, the bendable portion 3 can be rapidly bent in the right-hand and left-hand directions.

As described above, the bendable portion 3 can be bent by pulling two out of the four operating wires 51 to 54, and therefore the bendable portion can be properly bent in an intended direction without being twisted, even if the optical fiber bundles 95 and 96, the tube 97, etc., are asymmetrically disposed within the bendable portion 3. Further, upon angular movement of the operating shafts 61 and 62, the operating wires 51 to 54 can be pulled without any play (and hence any time lag) through the pulleys 71 to 74 or the pulleys 81 to 84, thus achieving an excellent operability.

Figure 8:
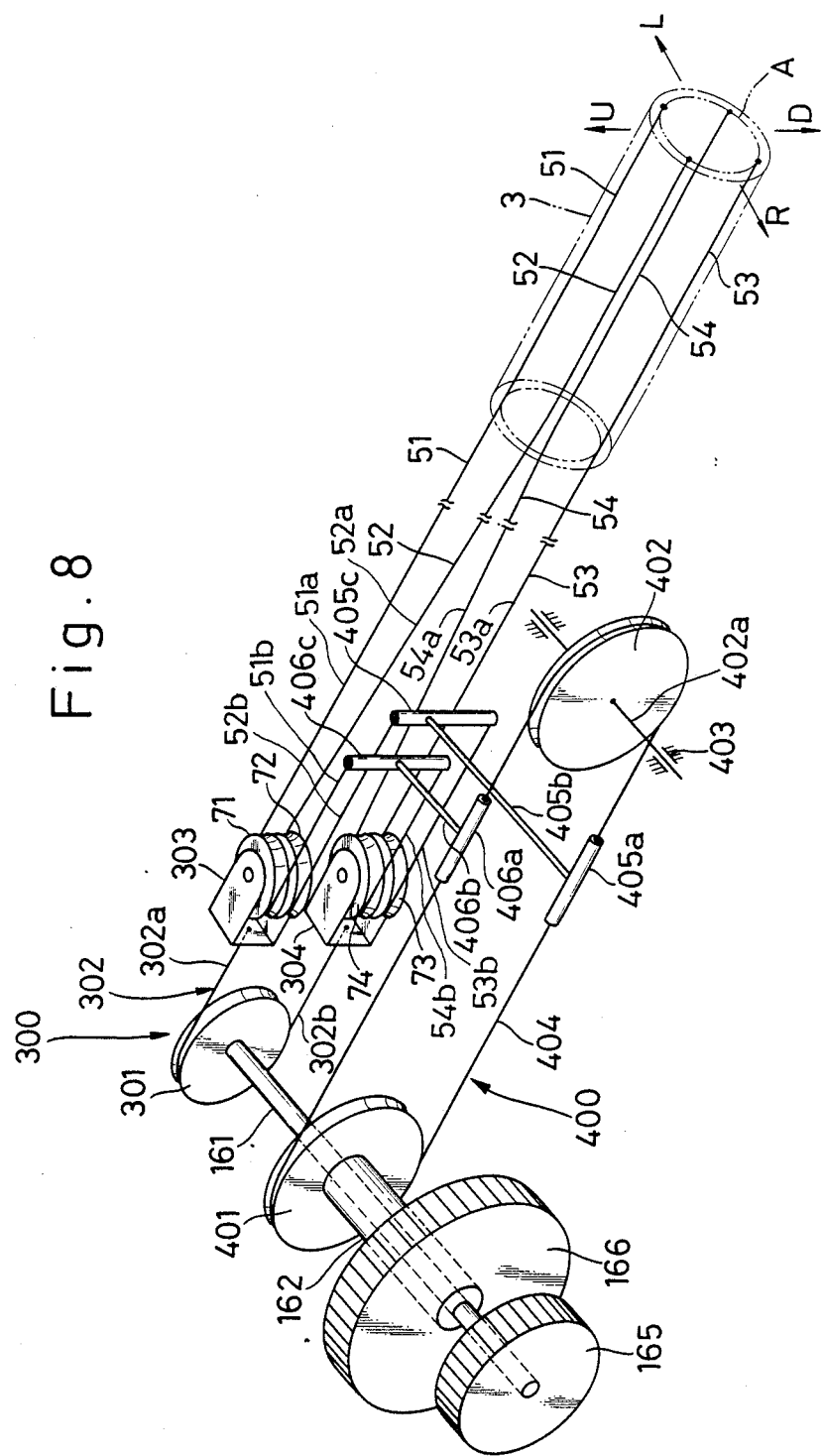

FIG. 8 shows a fifth embodiment of the invention. In this embodiment, two out of four operating wires 51 to 54 are pulled to bend the bendable portion 3 vertically and horizontally. More specifically, a first operating shaft 161 extends through and is rotatably borne by a sleeve-like second operating shaft 162. The second operating shaft 162 extends through a wall of a body of the endoscope and is rotatably borne by a bearing (not shown) mounted on the body. Manipulating knobs 165 and 166 are fixedly mounted respectively on one ends of the operating shafts 161 and 162 disposed exteriorly of the body. Pulleys 301 and 401 are fixedly mounted respectively on the other ends of the operating shafts 161 and 162 disposed within the body. A driving wire 302 is extended around the pulley 301, and is fixedly connected to that portion of the outer periphery of the pulley 301 remotest from the bendable portion. The driving wire 302 has parallel opposed upper and lower portions 302a and 302b extending from the pulley 301 toward the bendable portion 3. The ends of the two portions 302a and 302b remote from the pulley 301 are fixedly connected to support members 303 and 304, respectively. A pair of pulleys 71 and 72 are mounted on one support member 303 so as to be rotated independently of each other. The operating wires 51 and 52 are extended around the pulleys 71 and 72, respectively. Similarly, a pair of pulleys 73 and 74 are mounted on the other support member 304 so as to be rotated independently of each other. The operating wires 53 and 54 are extended around the pulleys 73 and 74, respectively. In this embodiment, the pulley 301, the driving wire 302 and the support members 303 and 304 jointly constitute a first connecting means 300 which operatively connects the first operating shaft 161 to the pulleys 71 to 74.

A shaft 402a is rotatably supported by bearings 403 disposed closer to the bendable portion 3 than the pulley 401, and a pulley 402 is fixedly mounted on the shaft 402a for rotation therewith, the pulley 402 being equal in diameter to the pulley 401 fixedly mounted on the second operating shaft 162. An endless driving wire 404 is extended around and between the two pulleys 401 and 402. The driving wire 404 is fixedly connected to the outer periphery of the pulley 401 at one point remotest from the pulley 402 and is also fixedly connected to the outer periphery of the pulley 402 at one point remotest from the pulley 401. The lower portion of the driving wire 404 is passed through and fixed to a tube 405a. A horizontal rod 405b extends perpendicular to the tube 405a and is fixedly connected at its one end to a central portion of the tube 405a. The other end of the rod 405b is fixedly connected to a vertical tube 405c intermediate opposite ends of the tube 405c. The proximal ends of the operating wires 52 and 53 are inserted into and fixedly connected to the opposite ends of the tube 405c, respectively. Similarly, a tube 406a is fixedly mounted on the upper portion of the driving wire 404, and a horizontal rod 406b is fixedly connected between the tube 406a and a vertical tube 406c. The proximal ends of the operating wires 51 and 54 are inserted into and fixedly connected to the opposite ends of the tube 406c, respectively. Although the rods 405b and 406b are shown as being relatively long for illustration purposes, these rods are actually relatively short, and can transmit forces from the tubes 405a and 406a to the tubes 405c and 406c, respectively, while being maintained generally vertically, that is, perpendicular to the axis of the insertion portion 2.

The pulleys 401 and 402, the driving wire 404, the tubes 405a, 405c, 406a and 406c and the rods 405b and 406b jointly constitute a second connecting means 400 which operatively connects the second operating shaft 162 to the pulleys 71 to 74.

The operating wires 51, 52, 53 and 54 have respective proximal leading portions 51a, 52a, 53a and 54a respectively extending between a wire guide and the pulleys 71, 72, 73 and 74, and respective turned-back portions 51b, 52b, 53b and 54b respectively extending between the pulleys 71 to 74 and the tubes 405c and 406c. The distal ends of the operating wires 51 to 54 are fixedly connected to the rigid portion 4 in the same manner as described above for the fourth embodiment of FIGS. 6 and 7.

In this fifth embodiment of FIG. 8, when the first operating shaft 161 is angularly moved in a counterclockwise direction with the second operating shaft 162 remaining stationary, the pulleys 71 and 72 are moved in a direction away from the bendable portion 3 through the pulley 301, the upper portion 302a of the driving wire 302 and the support member 303, so that the two operating wires 51 and 52 are pulled to bend the bendable portion 3 upwardly, that is, in a direction of an arrow U. On the other hand, when the first operating shaft 161 is angularly moved in the opposite direction, that is, in a clockwise direction, the pulleys 73 and 74 are moved away from the bendable portion 3, so that the two operating wires 53 and 54 are pulled to bend the bendable portion 3 downwardly, that is, in a direction of an arrow D.

When the second operating shaft 162 is angularly moved in a clockwise direction with the first operating shaft 161 remaining stationary, the proximal ends of the two operating wires 51 and 54 are moved toward the bendable portion 3 through the pulley 401, the driving wire 404, the tube 406a, the rod 406b and the tube 406c. As a result, the two operating wires 51 and 54 are pulled to bend the bendable portion 3 in a left-hand direction as indicated by an arrow L as viewed from the body. On the other hand, when the second operating shaft 162 is angularly moved in the opposite direction, that is, in a counterclockwise direction, the proximal ends of the two operating wires 52 and 53 are moved toward the bendable portion 3 through the pulley 401, the driving wire 404, the tube 405a, the rod 405b and the tube 405c. As a result, the two operating wires 52 and 53 are pulled to bend the bendable portion 3 in a right-hand direction as indicated by an arrow R as viewed from the body.

In this fifth embodiment, the pulleys 81 to 84 used in the fourth embodiment of FIG. 7 are not employed, and therefore the construction is simpler. Instead, only when the bendable portion 3 is moved upwardly and downwardly upon angular movement of the first operating shaft 161, the amount of movement of the proximal leading portions 51a to 54a of the operating wires 51 to 54 is twice the amount of movement of the pulleys 71 and 74 to thereby bend the bendable portion 3 rapidly.

A sixth embodiment of the invention shown in FIGS. 9 and 10 is rather similar to the fifth embodiment of FIG. 8. In this sixth embodiment, as shown in FIG. 10, although the distal ends of operating wires 51 to 54, fixedly connected to the rigid portion 4, are disposed in a circle A, these four fixed distal ends are not circumferentially spaced an angle of 90 degrees from one another. More specifically, the fixed distal ends of the operating wires 51 and 52 are spaced an equal distance Xa from a vertical line V passing through the axis or center line of the bendable portion 3. Also, the fixed distal ends of the operating wires 53 and 54 are spaced an equal distance Xb from the vertical line V. The distance Xb is greater than the distance Xa. Further, the fixed distal ends of the operating wires 51 and 52 are spaced an equal distance Ya from a horizontal line H passing through the axis of the bendable portion 3, and the fixed distal ends of the operating wires 53 and 54 are spaced an equal distance Yb from the horizontal line H. The distance Ya is greater than the distance Yb. This arrangement of the fixed distal ends of the operating wires 51 to 54 is employed in the case where the resistance to the upward bending of the bendable portion 3 is greater than the resistance to the downward bending of the bendable portion 3. Thus, with this arrangement, by applying substantially the same pulling force to the operating wires 51 to 54, the bendable portion 3 can be properly bent upwardly and downwardly.

A pair of pulleys 311 and 312 are fixedly mounted on a first operating shaft 161 for angular movement therewith. The ratio of the radius ra of the pulley 311 to the radius rb of the pulley 312 is equal to the ratio of the distance Ya (between the fixed distal ends of the operating wires 51 and 52 and the horizontal line H) to the distance Yb (between the fixed distal ends of the operating wires 53 and 54 and the horizontal line H). This relation is represented by the following formula:

$$ra:rb = Ya:Yb$$

A driving wire 313 is fixedly connected at one end to the outer periphery of the pulley 311, and extends from the upper side of the pulley 311 toward the bendable portion 3, and is fixedly connected at the other end thereof to a support member 303 which rotatably supports pulleys 71 and 72. A driving wire 314 is fixedly connected at one end to the outer periphery of the pulley 312, and extends from the lower side of the pulley 312 toward the bendable portion 3, and is fixedly connected at the other end thereof to a support member 304 which rotatably supports pulleys 73 and 74. The pulleys 311 and 312, the driving wires 313 and 314 and the support members 303 and 304 constitute a first connecting means 310 which operatively connects the first operating shaft 161 to the pulleys 71 to 74.

A pair of pulleys 411 and 412 are fixedly mounted on a second operating shaft 162 for angular movement therewith. The ratio of the radius ra' of the pulley 411 to the radius rb' of the pulley 412 is equal to the ratio of the distance Xa (between the fixed distal ends of the operating wires 51 and 52 and the vertical line V) to the distance Xb (between the fixed distal ends of the operating wires 53 and 54 and the vertical line V). This relation is represented by the following formula:

$$ra':rb' = Xa:Xb$$

Two pulleys 413 and 414, which are equal in diameter to the pulleys 411 and 412, respectively, are rotatably supported on the body and are disposed closer to the bendable portion 3 than the pulleys 411 and 412. An endless wire 415 is extended around and between the pulleys 411 and 413, and is fixedly connected at one point to the outer periphery of the pulley 411 and also fixedly connected at one point to the outer periphery of the pulley 413. An endless wire 416 is extended around and between the pulleys 412 and 414, and is fixedly connected at one point to the outer periphery of the pulley 412 and also fixedly connected at one point to the outer periphery of the pulley 414. The proximal end of the operating wire 54 is connected to the upper portion of the endless wire 415 through a rod 424, and the proximal end of the operating wire 53 is connected to the lower portion of the endless wire 415 through a rod 423.

The proximal end of the operating wire 51 is connected to the upper portion of the endless wire 416 through a rod 421, and the proximal end of the operating wire 52 is connected to the lower portion of the endless wire through a rod 422. Four tubes (not shown) are fitted on and fixed to the upper and lower portions of the endless wires 415 and 416, respectively, and one ends of the rods 421 to 424 are fixedly connected to central portions of these four tubes, respectively. The pulleys 411 to 414, the driving wires 415 and 416 and the rods 421 to 424 jointly constitute a second connecting means 410 which operatively connects the second operating shaft 162 to the pulleys 71 to 74.

In this sixth embodiment of FIG. 9, when the first operating shaft 161 is angularly moved in a counterclockwise direction, the pulleys 71 and 72 are moved in a direction away from the bendable portion 3 through the pulley 311, the driving wire 313 and the support member 303, so that the two operating wires 51 and 52 are pulled to bend the bendable portion 3 upwardly, that is, in a direction of an arrow U. On the other hand, when the first operating shaft 161 is angularly moved in the opposite direction, that is, in a clockwise direction, the pulleys 73 and 74 are moved away from the bendable portion 3 through the pulley 312, the driving wire 314 and the support member 304, so that the two operating wires 53 and 54 are pulled to bend the bendable portion 3 downwardly, that is, in a direction of an arrow D.

When the second operating shaft 162 is angularly moved in a clockwise direction, the proximal end of the operating wire 54 is moved toward the bendable portion 3 through the pulley 411, the driving wire 415 and the rod 424, and at the same time the proximal end of the operating wire 51 is also moved toward the bendable portion 3 through the pulley 412, the driving wire 416 and the rod 421. As a result, the operating wires 51 and 54 are pulled, so that the bendable portion 3 is bent in a left-hand direction L when viewed from the body. On the other hand, when the second operating shaft 162 is angularly moved in a counterclockwise direction, the proximal ends of the two operating wires 52 and 53 are moved toward the bendable portion 3, so that the operating wires 52 and 53 are pulled to bend the bendable portion 3 in a right-hand direction R when viewed from the body.

As described above, the distance Ya between the fixed distal ends of the operating wires 51 and 52 and the horizontal line H is greater than the distance Yb between the fixed distal ends of the operating wires 53 and 54 and the horizontal line H. Therefore, the ratio of the amount of movement of the operating wires 51 and 52 required to upwardly bend the bendable portion 3 by a given amount to the amount of movement of the operating wires 53 and 54 required to downwardly bend the bendable portion 3 by such a given amount is Ya/Yb. On the other hand, the ratio of the diameter ra of the pulley 311 to the diameter rb of the pulley 312 is Ya/Yb, and therefore when the first operating shaft 161 is angularly moved in the opposite directions by the same amount, the bendable portion 3 can be bent upwardly and downwardly by an equal amount.

As described above, the ratio of the radius ra' of the pulley 411 to the radius rb' of the pulley 412 is equal to the ratio of the distance Xa between the fixed distal ends of the operating wires 51 and 52 and the vertical line V to the distance Xb between the fixed distal ends of the operating wires 53 and 54 and the vertical line V. With this arrangement, the ratio between the amounts of simultaneous movement of the operating wires 51 and 54 upon angular movement of the second operating shaft 162 in a clockwise direction is equal to the ratio of Xa/Xb. Therefore, the bendable portion 3 can be accurately bent in the left-hand direction L. Similarly, the ratio between the amounts of simultaneous movement of the operating wires 52 and 53 upon angular movement of the second operating shaft 162 in a counterclockwise direction is equal to the ratio of Xa/Xb. Therefore, the bendable portion 3 can be accurately bent in the right-hand direction R.

A seventh embodiment of the invention shown in FIG. 11 is similar to the sixth embodiment of FIG. 9, and differs therefrom in that an arm 320 is fixedly mounted at its central portion on a first operating shaft 161, and in that pulleys 71 and 72 are mounted on the upper end of the arm 320 so as to be angularly moved independently of each other while pulleys 73 and 74 are mounted on the lower end of the arm 320 so as to be angularly moved independently of each other. The arm 320 constitutes a first connecting means which operatively connects the first operating shaft 161 to the pulleys 71 to 74. In accordance with the angular movement of the first operating shaft 161, the pulleys 71 to 74 are moved through the arm 320, so that the bendable portion 3 is bent upwardly and downwardly.

Figure 13:
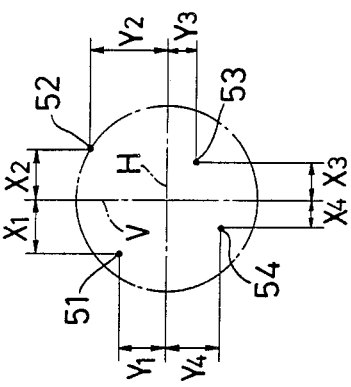
FIG. 13 is a schematic view showing the positions of fixed distal ends of four operating wires of the bending device of FIG. 12.
Figure 12:
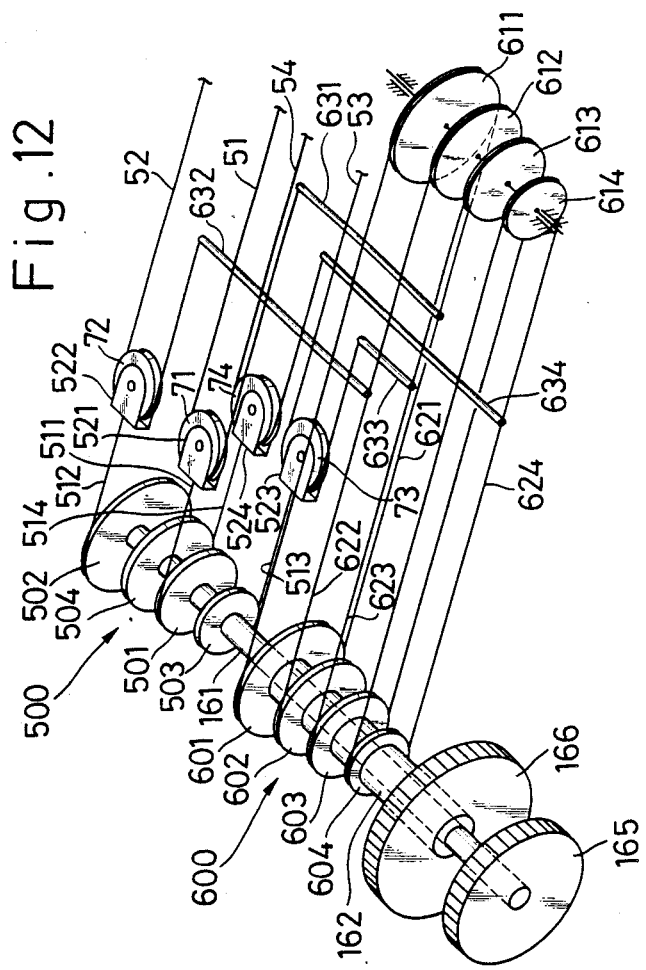

An eighth embodiment of the invention shown in FIGS. 12 and 13 is basically similar to the fifth embodiment of FIG. 8 and the sixth embodiment of FIG. 9, and differs therefrom in that the distances X1, X2, X3 and X4 between the fixed distal ends of operating wires 51 to 54 and a vertical line V are different from one another, and in that the distances Y1, Y2, Y3 and Y4 between the fixed distal ends of the operating wires 51 to 54 and a horizontal line H are different from one another, as shown in FIG. 13. A first connecting means 500, operatively connecting a first operating shaft 161 to pulleys 71 to 74, comprises four pulleys 501 to 504 fixedly mounted on the first operating shaft 161, four driving wires 511 to 514 respectively fixedly connected at their one ends to the pulleys 501 to 504, and four support members 521 to 524 to which the other ends of the driving wires 511 to 514 are fixedly connected, respectively. The ratio between the radii r1, r2, r3 and r4 of the pulleys 501 to 504 are represented by the following formula:

$$r1{:}r2{:}r3{:}r4 = Y1{:}Y2{:}Y3{:}Y4$$

A second connecting means 600, operatively connecting a second operating shaft 162 to the pulleys 71 to 74, comprises four pulleys 601 to 604 fixedly mounted on the second operating shaft 162, four pulleys 611 to 614 which are equal in diameter to the pulleys 601 to 604, respectively, and are disposed closer to the bendable portion 3 than the pulleys 601 to 604, four endless driving wires 621 to 624 respectively extended around and between the four pair of mating pulleys 601 to 604 and 611 to 614, rods 632 and 633 respectively connecting the upper portions of the driving wires 622 and 623 to the proximal ends of the operating wires 52 and 53, and rods 631 and 634 respectively connecting the lower portions of the driving wires 621 and 624 to the proximal ends of the operating wires 51 and 54. The ratio between the radii r1', r2', r3' and r4' of the pulleys 601 to 604 is represented by the following formula:

$r1':r2':r3':r4' = X1:X2:X3:X4$

The operation of this eighth embodiment of FIGS. 12 and 13 will be readily appreciated from the description of the sixth embodiment of FIGS. 9 and 10, and therefore will now be described briefly here. By angularly moving the first operating shaft 161, the bendable portion 3 can be accurately bent upwardly and downwardly. When the first operating shaft 161 is angularly moved in the opposite directions by the same given amount, the amount of the upward bending of the bendable portion 3 is equal to the amount of downward bending thereof. On the other hand, by angularly moving the second operating shaft 162, the bendable portion 3 can be accurately bent in right-hand and left-hand directions. When the second operating shaft 162 is angularly moved in the opposite directions by the same given amount, the amount of the right-hand bending of the bendable portion 3 is equal to the amount of the left-hand bending thereof.

In the first and second connecting means of the above embodiments of FIGS. 8 to 13, the pulleys may be replaced by sprockets, and the driving wires may be replaced by chains.

What is claimed is:

1. An endoscope comprising:
   (a) a body;
   (b) a hollow insertion portion extending from said body;
   (c) a hollow elongated bendable portion extending from a forward end of said insertion portion remote from said body; and
   (d) means for bending said bendable portion, said bending means comprising:
   (i) a pair of operating wires having their proximal ends disposed within said body, said two operating wires extending through said insertion portion into said bendable portion and fixedly connected at their distal ends to a distal end of said bendable portion remote from said insertion portion, said fixed distal ends of said two operating wires being spaced from each other generally peripherally of said bendable portion;
   (ii) an operating shaft mounted on said body for angular movement about an axis thereof;
   (iii) an manipulating member for angularly moving said operating shaft;
   (iv) a pair of engaging members provided at said body, said pair of operating wires being extended respectively around said pair of engaging members to be turned back toward said bendable portion;
   (v) retainer means retaining the proximal ends of said pair of operating wires; and
   (vi) connecting means operatively connecting said operating shaft to said pair of engaging members so that when said operating shaft is angularly moved in one direction, one of said pair of engaging members can be moved away from said bendable portion, with the other engaging member being moved toward said bendable portion, so as to pull said operating wire, associated with said one engaging member, away from said bendable portion, thereby bending said bendable portion in one direction; when said operating shaft is angularly moved in the other direction, said other engaging member being moved away from said bendable portion through said connecting means, with said one engaging member being moved toward said bendable portion, so as to pull said operating wire, associated with said other engaging member, away from said bendable portion, thereby bending said bendable portion in another direction.

2. An endoscope according to claim 1, in which said connecting means comprises an angularly movable member fixedly mounted on said operating shaft for angular movement therewith about the axis of said operating shaft, said pair of engaging members being mounted on said angularly movable member and disposed in diametrically opposite relation to each other with respect to said operating shaft.

3. An endoscope according to claim 1, in which said connecting means comprises a pinion fixedly mounted on said operating shaft for angular movement therewith, and a pair of racks in mesh respectively with the opposite sides of said pinion so as to move in opposite directions generally along the axis of said insertion portion, each of said two engaging members being mounted on a respective one of said two racks for movement therewith.

4. An endoscope according to claim 1, in which said connecting means comprises an angularly movable member fixedly mounted on said operating shaft for angular movement therewith about the axis of said operating shaft, and a pair of flexible elongated members connected at their one ends to said angularly movable member, said pair of engaging members being connected respectively to the other ends of said two flexible elongated members.

5. An endoscope according to claim 1, in which said retainer means comprises a pair of stop members each disposed between said engaging members and said insertion portion and having a hole formed therethrough and extending generally in the direction of the axis of said insertion portion, and a pair of sliders received respectively in said holes of said stop members so as to slidingly move therealong, the proximal ends of said two operating wires being fixedly connected respectively to said two sliders, each of said sliders having a projection on its outer surface for abutment with a respective one of said sliders so as to prevent said slider from movement toward said engaging member, and said retainer means also including a pair of springs respectively urging said sliders away from said engaging members.

6. An endoscope comprising:
   (a) a body;
   (b) a hollow insertion portion extending from said body;
   (c) a hollow elongated bendable portion extending from a forward end of said insertion portion remote from said body; and
   (d) means for bending said bendable portion, said bending means comprising:
   (i) first to fourth operating wires having their proximal ends disposed within said body, said four operating wires extending through said insertion portion into said bendable portion and fixedly connected at their distal ends to a distal end of said bendable portion remote from said insertion portion, said fixed distal ends of said first to fourth operating wires being spaced from one another peripherally of said bendable portion and arranged in this order;
   (ii) a pair of first and second operating shafts mounted on said body for angular movement about their axes;

(iii) a pair of first and second manipulating members for angularly moving said first and second operating shafts, respectively;

(iv) first to fourth main engaging members provided at said body, said first to fourth operating wires being extended respectively around said first to fourth main engaging members to be turned back toward said bendable portion to provide four turned-back portions defined respectively by the proximal end portions of said four operating wires, respectively;

(v) first connecting means operatively connecting said first operating shaft to said four main engaging members so that when said first operating shaft is angularly moved in one direction, said first and second engaging members are moved away from said bendable portion so as to simultaneously pull said first and second operating wires away from said bendable portion, thereby bending said bendable portion in a first direction; when said first operating shaft is angularly moved in the other direction, said third and fourth engaging members being moved away from said bendable portion through said first connecting means so as to simultaneously pull said third and fourth operating wires away from said bendable portion, thereby bending said bendable portion in a second direction opposite to said first direction; and (vi) second connecting means operatively connecting said second operating shaft to said four turned-back portions so that when said second operating shaft is angularly moved in one direction, said turned-back portions of said first and fourth operating wires are moved toward said bendable portion so as to simultaneously pull said first and fourth operating wires away from said bendable portion, thereby bending said bendable portion in a third direction generally perpendicular to said first and second directions; when said second operating shaft is angularly moved in the other direction, said turned-back portions of said second and third operating wires being moved toward said bendable portion through said second connecting means so as to simultaneously pull said second and third operating wires away from said bendable portion, thereby bending said bendable portion in a fourth direction opposite to said third direction.

7. An endoscope according to claim 6, in which said bending means further comprises a retainer means retaining the proximal ends of said four operating wires, and first to fourth auxiliary engaging members around which said turned-back portions of said first to fourth operating wires are extended, respectively, so that said four turned-back portions respectively have first turned-back sections extending respectively between said main engaging members and said auxiliary engaging members and second turned-back sections extending respectively between said auxiliary engaging members and said retainer means, said second connecting means being operable so that when said second operating shaft is angularly moved in the one direction, said first and fourth auxiliary engaging members are moved toward said bendable portion so as to move said first and fourth operating wires away from said bendable portion to bend the same in said third direction; when said second shaft is angularly moved in the other direction, said second and third auxiliary engaging members being moved toward said bendable portion so as to move said second and third operating wires away from said bendable portion to bend the same in said fourth direction.

8. An endoscope according to claim 6, in which said second connecting means operatively connects said second operating shaft to the proximal ends of said four operating wires, so that when said second operating shaft is angularly moved in the one direction, the proximal ends of said first and fourth operating wires are moved toward said bendable portion with the proximal ends of said second and third operating wires being moved away from said bendable portion, thereby bending said bendable portion in said third direction; when said second operating shaft is angularly moved in the other direction, the proximal ends of said second and third operating wires are moved toward said bendable portion with the proximal ends of said first and fourth being moved away from said bendable portion, thereby bending said bendable portion in said fourth direction.

9. An endoscope according to claim 6, in which the fixed distal ends of said four operating wires are disposed in a plane perpendicular to the axis of said bendable portion, first and second straight lines being disposed in said plane and perpendicularly intersecting each other at the axis of said bendable portion, the ratio between the respective amounts of movement of said four operating wires per unit angular movement of said first operating shaft to be effected through said first connecting means being equal to the ratio between the respective distances between the fixed distal ends of said four operating wires and said first straight line, and the ratio between the respective amounts of movement of said four operating wires per unit angular movement of said second operating shaft to be effected through said second connecting means being equal to the ratio between the respective distances between the fixed distal ends of said four operating wires and said second straight line.

* * * * *